United States Patent [19]
Zamoyski

[11] Patent Number: 5,952,219
[45] Date of Patent: Sep. 14, 1999

[54] APPARATUS FOR CULTURING AND HARVESTING FUNGAL SPORES

[76] Inventor: Mark Zamoyski, 988 Foothill Dr., San Jose, Calif. 95123

[21] Appl. No.: 09/135,268

[22] Filed: Aug. 17, 1998

[51] Int. Cl.[6] ................................................. C12M 3/00
[52] U.S. Cl. ................................. 435/297.2; 435/305.1; 435/308.1
[58] Field of Search .................................. 422/102, 104; 435/288.3, 289.1, 297.1, 297.2, 305.1, 308.1

[56] References Cited

U.S. PATENT DOCUMENTS 3,062,724  11/1962  Reusser .
4,377,639  3/1983  Lee ............................................ 435/285
5,219,390  6/1993  McClane .................................. 73/864

Primary Examiner—David A. Redding

[57] ABSTRACT

An apparatus for culturing and harvesting fungal spores and airborne particulates made up of a culture chamber with a means of issuing positive air pressure attached to one side and a harvesting chamber attached to the opposite side with means of dissipating the positive air pressure and means of collecting fungal spores and mycotoxins. Also a hydrophilic culture device made up of a plurality or horizontal and vertical planar members residing in a pan that can be inserted in the culture chamber.

6 Claims, 2 Drawing Sheets

APPARATUS FOR CULTURING AND HARVESTING FUNGAL SPORES

BACKGROUND

1. Field of Invention

This invention relates generally to devices and methods for use in culturing and harvesting spores and other airborne particulates produced by fungi and more specifically to a device for growing and harvesting spores and airborne particulates for hydrophilic types of fungi which need conditions close to saturation to grow and produce spores.

2. Description of Prior Art

Most methods and devices today focus on detection, prevention or eradication of fungi. Fungi can cause infectious disease, allergic disease, and toxic disease. Fungi can grow on any carbon source when sufficient moisture is present.

Fungi produce mycotoxins (substances with direct toxicity for humans and animals that are secreted directly into the environment). Mycotoxins are a secondary chemical matabolite and may be contained in the spores or other airborne fragments produced by the fungi. Mycotoxin effects range from "Sick Building Syndrome" (SBS) to death.

Stachybotrys atra (also called Stachybotrys chartarum) is a hydrophilic fungus that grows on cellulose based materials and its spores contain powerful mycotoxins.

A cluster of 10 cases of pulmonary hemorrhage/hemosiderosis (bleeding in the lungs) occurred between January 1993 and December 1994 among the infants in one particular area of Cleveland where water soaked cellulose based building materials in some homes created an environment where Stachybotrys atra grew. Hemorrhaging recurred in five infants after returning home from the hospital and one infant died. The mean age of the infants was 10.2 weeks and the pulmonary hemosiderosis disorder linked to Stachybotrys atra was limited to infants in the households. The EPA and Cleveland Department of Health now believe the fungus is responsible for the cluster of acute pulmonary hemolysis/hemosiderosis that has claimed the lives of 9 infants between 1993 and the present.

It may not be obvious why it would be desirable to build an apparatus to mass produce spores and mycotoxins of fungi such as Stachybotrys atra however the same mycotoxins that killed the young infants hold the key for a highly specific treatment for cancer. Physiologically, young infants and cancer are very similar. Both are undergoing rapid tissue growth and angiogenesis (the construction of new blood vessels to supply the tissue with nutrients and oxygen). Since Stachybotrys atra mycotoxins interfere with the construction of new blood vessel they can be a highly specific treatment to stop the growth of cancer. Large quantities of the spores and mycotoxins will be required for further research, refinement, and treatment purposes.

It is thus the intent of this invention to provide an apparatus and method for producing and harvesting large quantities of fungal spores and mycotoxins, particularly from hydrophilic fungi such as Stachybotrys atra.

SUMMARY OF INVENTION

It is an object of the invention to provide an apparatus and method for producing and harvesting large quantities of fungal spores and mycotoxins.

Another object is to provide an apparatus and method of producing and harvesting large quantities of fungal spores and mycotoxins from hydrophilic fungi.

Another object is to provide an apparatus capable of generating the large amount of fungal spore and mycotoxin material that will be required for research, refinement, and treatment of cancer and for other medicinal purposes.

In accordance with the invention a three compartment device, the first compartment with means for issuing periodic air streams or positive air pressure across the second compartment and on into the third compartment, the second compartment containing the culture medium with active fungal growth, and the third compartment with means of dissipating or venting said positive air pressure and means of collecting harvested airborne particulates into a container.

Also in accordance with the invention a device for supporting and providing saturation to a plurality of culture medium members comprising a pan as a base member with means of receiving a relatively planar slotted horizontal member into which slots are inserted a plurality of vertical relatively planar culture medium members, which in turn are inserted at other end into another horizontal slotted member.

STATIC DESCRIPTION OF INVENTION

Figure 1:
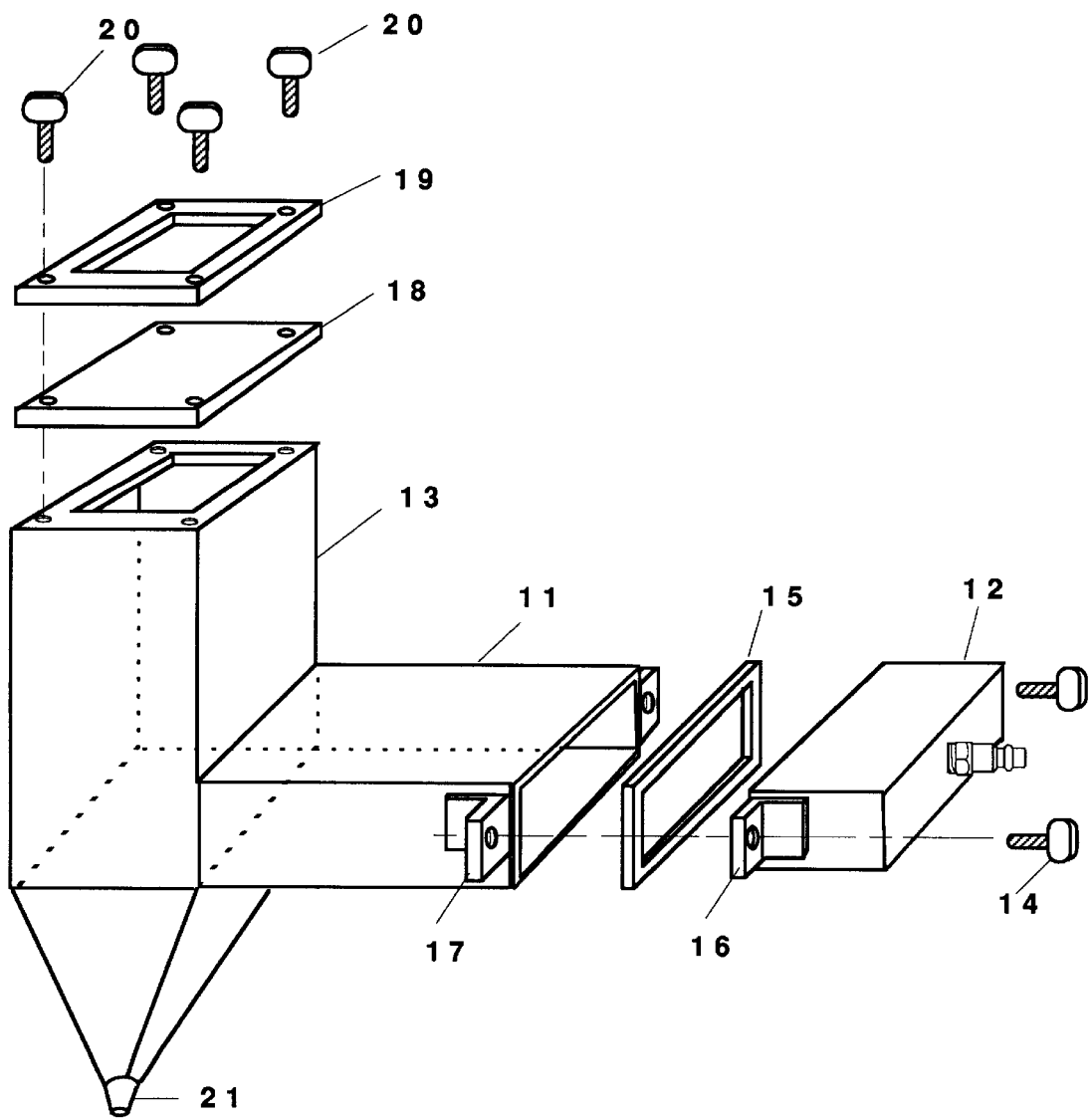
FIG. 1 is a perspective view illustrating the main members of a device for growing and harvesting fungal spores and airborne particulates in accordance with the present invention.

In accordance with the preferred embodiment of the present invention FIG. 1 shows a device comprised of a culture chamber 11 to which is attached a means of issuing periodic positive air pressure 12 on one side and to which is attached a harvesting chamber 13 on the other side.

The means of periodically issuing positive air pressure 12 may use air provided from an external source such as a compressor or include internal sources such as fans or any other device suitable for the purpose and may also include any control or timing circuitry and devices suitable for the purpose and may also include directional and intensity control for the air streams. In the preferred embodiment the means of issuing positive air pressure 12 are attached to the culture chamber 11 with conventional fasteners 14, gasket 15, and attachment brackets 16 and 17 however an suitable hardware or means of attachment may be used. Other embodiments of means of issuing periodic positive air pressure 12 may also include means of introducing spores so that the first periodic air burst or bursts may act to disseminate the spores onto the culture medium.

The preferred embodiment of the culture chamber 11 is a relatively rectangular design however other embodiments may include any suitable geometry and may include any suitable means for securing or stabilizing a culture medium that is placed within it as well as also provide means for monitoring and adding moisture content or nutrients to the culture medium. The preferred embodiment of the culture chamber 11 is constructed from plastic however glass, metal, or any other suitable material may be used.

The preferred embodiment of the harvester chamber 13 extends both upwards and downward. A filter element 18 is attached to the upper end by a filter bracket 19 and conventional fasteners 20 however any suitable means of attaching the filter may be used. The lower end of the harvester chamber 13 tapers down to a means of attaching a collection container 21. In the preferred embodiment the container attachment means 21 is a relatively conical end to which a container such as a test tube may be attached by pressure however any suitable geometry and means for of attaching a container may be employed including a relatively cylindrical threaded spout, clamping, latching or any other suitable means. The preferred embodiment of the harvester chamber 13 relies on gravity alone to precipitate airborne particulates other embodiments may include vibrational or electrostatic means to facilitate migration or precipitation of spores toward container attachment means 21. In preferred embodiment of the harvester chamber 13 is constructed from plastic however glass, metal, or any other suitable material may be used.

Figure 2A:
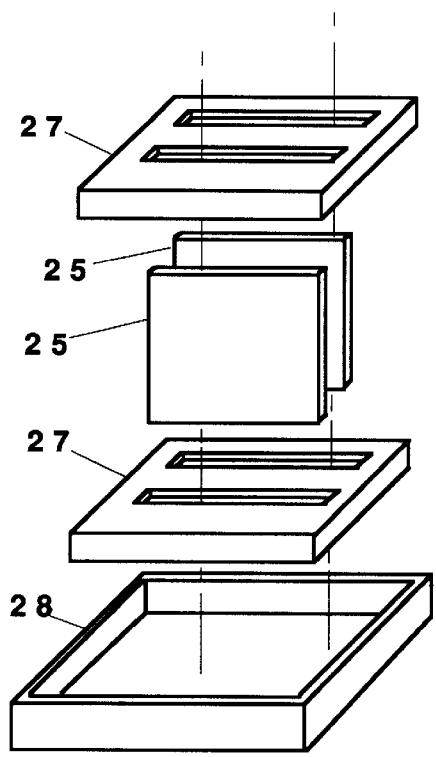
FIGS. 2A and 2B are perspective views of two embodiments of a high density hydrophilic culture medium device constructed in accordance with the present invention.
Figure 2B:
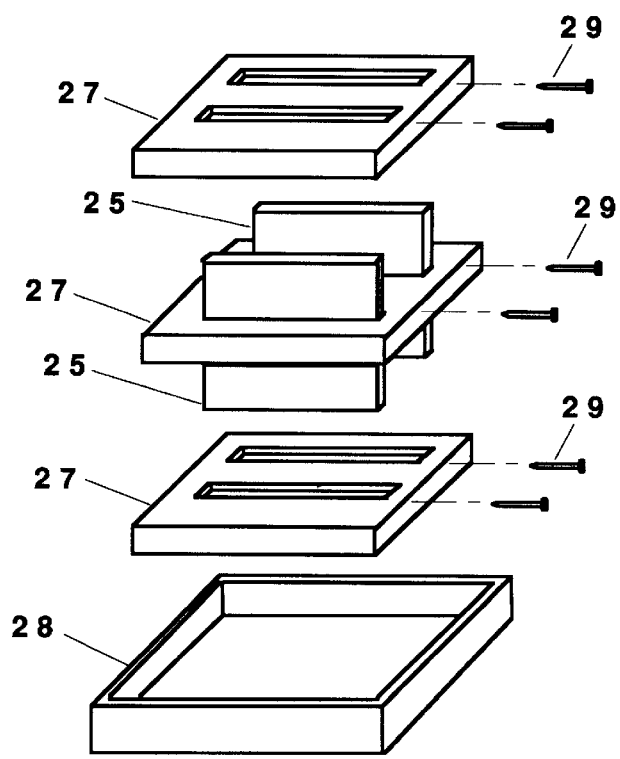

In accordance with the preferred embodiment of the present invention FIG. 2A shows a device for holding a plurality of culture medium members in an aqueous solution for insertion into culture chamber 11. The device is comprised of a plurality of vertical substantially planar members 25 that are inserted through slots or openings in a substantially planar horizontal member 27 at the lower end and inserted through another substantially planar horizontal member 27 at the upper end to define a structural frame which can then be inserted into a base pan member 28. FIG. 2B shows another embodiment which is the same as that of FIG. 2A with the exception that additional substantially planar horizontal members 27 can be used along the length of the substantially planar vertical members and that fasteners 29 may be used to additionally secure the vertical and horizontal members. In the preferred embodiment the base pan 28 is made from plastic and the vertical 25 members and horizontal members 27 are made of a cellulose based material capable of osmotically drawing up water however any suitable materials or culture mediums may be used and may already be impregnated with fungal spores. In the preferred embodiment the vertical and horizontal planar members are held in place by pressure against each other, however fasteners such as nails, screws, staples, adhesives, or any other means suitable may be used.

OPERATIONAL DESCRIPTION OF INVENTION

The various elements of the invention interact as follow. The means of issuing positive air pressure 12 issues periodic air streams or bursts through the culture chamber 11 where the culture medium resides. The motion of the air acts as an "air broom" sweeping the spores and other airborne particles from the culture medium chamber 11 into the harvesting chamber 13. The harvesting chamber 13 dissipates the positive air pressure both by its volume and through the filter element 18 located at the top. The filter element does not allow spores or airborne particulates to pass. Gravity acts to precipitate the airborne spores and particulates toward the bottom of the harvesting chamber where they are collected.

Water or a nutrient solution is poured into the base pan 28 of the culture medium device. The vertical culture medium members 25 extend downward through the lower slotted horizontal member 27 and into the water or nutrient solution. The water or nutrient solution is drawn up by osmosis into the culture medium. The lower slotted member 27 also acts to prevent spores from falling into the water while the culture medium is in the culture chamber 11. When the culture medium device of FIG. 2A or FIG. 2B is placed into the culture chamber 11 in FIG. 1 the geometry of the culture medium device acts as a air channel focusing air streams from the means of issuing positive air pressure 12 over the fungal cultures and into the harvesting chamber 13.

CONCLUSIONS, RAMIFICATIONS, AND SCOPE OF INVENTION

The fungal spore culturing and harvesting device of the invention anticipates the emerging need for production of large quantities of fungal spores and related mycotoxins for research and treatment of cancer and other medicinal purposes. While my above descriptions contain many specifications, these should not be construed as limitations on the scope of the invention, but rather as an exemplification of one preferred embodiment. Many other variations and uses are possible including harvesting products produced by a variety of other organisms for a variety of reasons.

Accordingly, the scope of the invention should be determined not by the embodiment(s) illustrated, but by the appended claims and their legal equivalents.

I claim:

1. A device for culturing and harvesting fungal spores and particulates comprising:

a) a culture chamber having a first open end attached to a means of issuing positive air pressure and an opposite open end;

b) a harvesting chamber attached to said opposite open end of said culture chamber;

c) said harvesting chamber having a open upper end to which a filter is attached and a tapered, lower end having means for attaching a container.

2. A hydrophilic culture device comprising:

a) a plurality of vertical substantially planar members, each passing through openings in a plurality of horizontal substantially planar members;

b) said vertical substantially planar members attached to said horizontal substantially planar members so as to define a structural frame;

c) a base pan member into which said structural frame is inserted.

3. A device as defined in claim 2 wherein said vertical substantially planar members are also attached to a substantially planar horizontal member at each end.

4. A device as defined in claim 2 wherein said vertical substantially planar members are attached to said substantially planar horizontal members by fasteners.

5. A device as defined in claim 2 wherein said vertical substantially planar members and said horizontal substantially planar members comprise cellulose based material.

6. An apparatus for production and harvesting of fungal spores and particulates comprising a device as defined in claim 1 wherein a device as defined in claims 2 through 5 is inserted into said culture chamber of claim 1.

* * * * *